(12) United States Patent
Johns et al.

(10) Patent No.: US 6,274,593 B1
(45) Date of Patent: Aug. 14, 2001

(54) SUBSTITUTED TETRAHYDRO ISOQUINOLINES AS MODULATORS OF DOPAMINE D3 RECEPTORS

(75) Inventors: Amanda Johns, Bishop's Stortford; David John Nash, Little Walden; Geoffrey Stemp, Bishop's Stortford, all of (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/403,893

(22) PCT Filed: Apr. 27, 1998

(86) PCT No.: PCT/EP98/02582

§ 371 Date: Oct. 27, 1999

§ 102(e) Date: Oct. 27, 1999

(87) PCT Pub. No.: WO98/50363

PCT Pub. Date: Nov. 12, 1998

(30) Foreign Application Priority Data

May 1, 1997 (GB) .................................................. 9708805

(51) Int. Cl.[7] ........................ A61K 31/47; C07D 217/06
(52) U.S. Cl. ............................................ 514/307; 546/146
(58) Field of Search .............................. 514/307; 546/146

(56) References Cited

U.S. PATENT DOCUMENTS

| | | |
|---|---|---|
| 4,220,778 | 9/1980 | Ellefson . |
| 4,925,850 | 5/1990 | George . |
| 5,294,621 | 3/1994 | Russell . |
| 5,350,754 | 9/1994 | Crawley . |
| 5,688,950 | 11/1997 | Chen . |
| 5,891,877 | 4/1999 | Brocchini . |

FOREIGN PATENT DOCUMENTS

| | | |
|---|---|---|
| 0 007 070 | 1/1980 | (EP) . |
| 051 190 A2 | 5/1982 | (EP) . |
| 0 300 865 A | 1/1989 | (EP) . |
| 0 431 580 A | 6/1991 | (EP) . |
| 0 464 846 A1 | 1/1992 | (EP) . |
| 0 494 623 A1 | 7/1992 | (EP) . |
| 2706895 | 12/1994 | (FR) . |
| 07070135 A | 3/1995 | (JP) . |
| WO 93/03025 | 2/1993 | (WO) . |
| WO 93/13105 | 7/1993 | (WO) . |
| WO 93/20099 | 10/1993 | (WO) . |
| WO 94/01408 | 1/1994 | (WO) . |
| WO 94/03426 | 2/1994 | (WO) . |
| WO 94/21628 | 9/1994 | (WO) . |
| WO 94/24129 | 10/1994 | (WO) . |
| WO 95/00508 | 1/1995 | (WO) . |
| WO 95/05363 | 2/1995 | (WO) . |
| WO 95/10513 | 4/1995 | (WO) . |
| WO 95/16674 | 6/1995 | (WO) . |
| WO 95/21165 | 8/1995 | (WO) . |
| WO 95/21832 | 8/1995 | (WO) . |
| WO 95/22542 | 8/1995 | (WO) . |
| WO 96 02245 A | 2/1996 | (WO) . |
| WO 96/09286 | 3/1996 | (WO) . |
| WO 96/11007 | 4/1996 | (WO) . |
| WO 96/20179 | 7/1996 | (WO) . |
| WO 96/20180 | 7/1996 | (WO) . |
| WO 96/20190 | 7/1996 | (WO) . |
| WO 96/30333 | 10/1996 | (WO) . |
| WO 97/00243 | 1/1997 | (WO) . |
| WO 97/11070 | 3/1997 | (WO) . |
| WO 98/49145 | 5/1997 | (WO) . |
| WO 98/51671 | 5/1997 | (WO) . |
| WO 97/28166 | 8/1997 | (WO) . |
| WO 97/29079 | 8/1997 | (WO) . |
| WO 97/40015 | 10/1997 | (WO) . |
| WO 97 43262 A | 11/1997 | (WO) . |
| WO 97/43262 | 11/1997 | (WO) . |
| 97/43262 | * 11/1997 | (WO) . |
| WO 97/47602 | 12/1997 | (WO) . |
| WO 98 06699 | 2/1998 | (WO) . |
| WO 98/07421 | 2/1998 | (WO) . |
| WO 98/23593 | 6/1998 | (WO) . |
| WO 98/48784 | 11/1998 | (WO) . |
| WO 98/50364 | 11/1998 | (WO) . |
| WO 98/52923 | 11/1998 | (WO) . |
| 8106903 | 2/1983 | (ZA) . |

OTHER PUBLICATIONS

Jerzy L. Mokrosz et al., "8–[4–[2–(1,2,3,4–Tetrahydroisoquinolinyl)]butyl]–8azaspiro[4.5]decane–7,9–dione: A new 5–HT1A Receptor Ligand with the same activity Profile as Buspirone", Journal of Medicinal Chemistry., vol. 39, No. 5, 1996, pp. 1125–1129, XP002074949.

I. Boyfield et al. Bioorg. Med. Chem. Lett., 1997, vol. 7 (15), 1995–1998.

AA Patsenko et al. Chemical Abstracts, vol. 107, No. 11, Sep. 14, 1987, Abstract No. 089337.

LM Jerzy et al., J. Med. Chem., vol. 39 (5) 1996) 1125–1129.

* cited by examiner

*Primary Examiner*—D. Margaret Seaman
(74) *Attorney, Agent, or Firm*—Nora Stein-Fernandez; Stephen Venetianer; Charles M. Kinzig

(57) ABSTRACT

The present invention provides compounds of formula (I):

Formula (I)

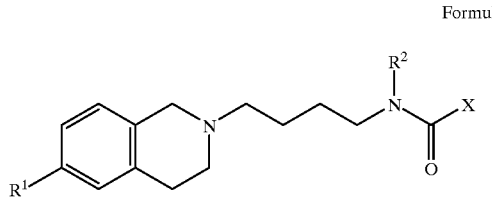

which are useful as antipsychotic agents.

11 Claims, No Drawings

SUBSTITUTED TETRAHYDRO ISOQUINOLINES AS MODULATORS OF DOPAMINE D3 RECEPTORS

The present invention relates to novel tetrahydroisoquinoline derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

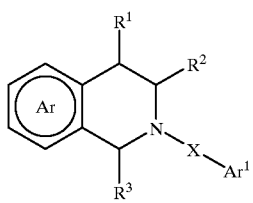

wherein

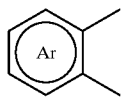

is an optionally substituted thienyl or optionally substituted phenyl ring; $R^1$, $R^2$ and $R^3$ are each inter alia hydrogen; X is inter alia $(CH_2)mNR^7CO$; m is 2–4; and $Ar^1$ is an optionally substituted heterocyclic ring or an optionally substituted phenyl ring. The compounds are said to be useful as antiarrhythmic agents.

We have now found a class of tetrahydroisoquinoline derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

Formula (I)

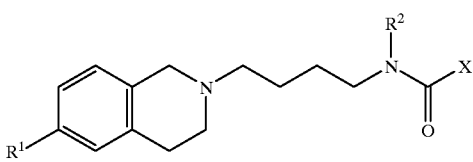

wherein:
$R^1$ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamido, $C_{1-4}$alkylsulphonamido$C_{1-4}$alkyl, $C_{1-4}$alkylamido$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group;

a group $R^3OCO(CH_2)p$, $R^3CON(R^4)(CH_2)_p$, $R^3R^4NCO(CH_2)_p$ or $R^3R^4NSO_2(CH_2)_p$ where each of $R_3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^3$—Z, wherein $Ar^3$ represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

X represents a group of the formula (a) or (b):

(a)

(b)

wherein

Ar and $Ar^1$ each independently represent an optionally substituted phenyl ring or an optionally substituted 5- or 6-membered aromatic heterocyclic ring; and Y represents a bond, —NHCO—, —CONH—, —$CH_2$—, or —$(CH_2)_mY^1(CH_2)_n$—, wherein $y^1$ represents O, S, $SO_2$, or CO and m and n each represent zero or 1 such that the sum of m+n is zero or 1;

$Ar^2$ represents an optionally substituted phenyl ring or an optionally substituted 5- or 6-membered aromatic heterocyclic ring; or an optionally substituted bicyclic ring system;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

Examples of compounds of formula (I) include those in which $Ar^2$ is a bicyclic aromatic or heteroaromatic ring system and in which $R^1$ is other than pentafluoroethyl.

When $R^1$ represents an aryl$C_{1-4}$alkoxy, arylsulphonyl, arylsulphonyloxy, arylsulphonyl$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety may be selected from an optionally substituted phenyl ring or an optionally substituted 5- or 6-membered heterocyclic ring. In the group $R^1$ an aryl moiety may be optionally substituted by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$alkanoyl, or $R^5R^6NCO$ where each of $R^5$ and $R^6$ independently represents a hydrogen atom or $C_{1-4}$alkyl group.

A halogen atom present in the compounds of formula (I) may be fluorine, chlorine, bromine or iodine.

An optionally substituted 5- or 6-membered heterocyclic aromatic ring, as defined for any of the groups Ar, $Ar^1$, $Ar^2$ or $Ar^3$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl and pyrazolyl.

Examples of bicyclic, for example bicyclic aromatic or heteroaromatic, ring systems for $Ar^2$ include naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl,cinnolinyl, isoquinolinyl, pyrazolo[1,5-a]pyrimidyl, pyrrolo[3,2-b]pyridyl, pyrrolo[3,2-c]lpyridyl, thieno[3,2-b]thiophenyl, 1,2-dihydro-2-oxo-quinolinyl, 2,3-dihydro-3-oxo-4H-benzoxazinyl, 1,2-dihydro-2-oxo-3H-indolyl.

The rings Ar, $Ar^1$, or $Ar^2$ may each independently be optionally substituted by one or more substituents selected from: a hydrogen or halogen atom, or a hydroxy, oxo, cyano, nitro, $C_{1-4}$alkyl, $C_{1-4}$alkoxy, $C_{1-4}$alkylenedioxy, $C_{1-4}$alkanoyl, $C_{1-4}$alkylsulphonyl, $C_{1-4}$alkylsulphinyl, $C_{1-4}$alkylthio, $R^7SO_2N(R^8)$—, $R^7R^8NSO_2$—, $R^7R^8N$—, $R^7R^8NCO$—,or $R^7CON(R^8)$— group wherein each of $R^7$ and $R^8$ independently represents a hydrogen atom or a $C_{1-4}$ alkyl group, or $R^7R^8$ together form a $C_{3-6}$ alkylene chain.

Alternatively, $Ar^1$ and $Ar^2$ may be optionally substituted by one or more 5- or 6-membered heterocyclic rings, as defined above, optionally substituted by a $C_{1-2}$ alkyl or $R^7R^8N$— group; wherein $R^7$ and $R^8$ are as defined above.

In the rings $Ar^1$ and $Ar^2$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulphuric, nitric or phosphoric acid; and organic acids ea. succinic, maleic, acetic, fumaric, citric, tartaric, benzoic, p-toluenesulphonic, methanesulphonic or naphthalenesulphonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

For compounds of formula (I) where A represents a group (b), trans geometry of the double bond is preferred.

In compounds of formula (I), it is preferred that $R^1$ represents a substituent selected from: a halogen atom, methyl, cyano, trifluoromethylsulfonyloxy, trifluoromethyl, pentafluoroethyl, or trifluoromethoxy group.

It is also preferred that the rings Ar, $Ar^1$, or $Ar^2$ are each independently optionally substituted by one or more substituents selected from: a hydrogen or halogen atom, cyano, methoxy, methylenedioxy, acetyl, acetylamino, methylsulfonyl, methylsulfonyloxy, methylaminosulfonyl, methylsulfonylamino, or methylaminocarbonyl group.

Certain of the substituted heteroaromatic ring systems included in compounds of formula (I) may exist in one or more tautomeric forms. The present invention includes within its scope all such tautomeric forms, including mixtures.

Particular compounds according to the invention include:
(E)-2-(4-(3-(2-Naphthyl)propenoyl)aminobutyl)-6-trifluoromethoxy-1,2,3,4-tetrahydroisoquinoline
(E)-2-(4-(3-(5-Indolyl)propenoyl)aminobutyl)-6-trifluoromethoxy-1,2,3,4-tetrahydroisoquinoline
(E)-2-(4-(3-(5-Benzimidazolyl)propenoyl)aminobutyl)-6-trifluoromethoxy-1,2,3,4-tetrahydroisoquinoline
(E)-2-(4-(3-(5-Indolyl)propenoyl)aminobutyl)-6-trifluoromethyl-1,2,3,4-tetrahydroisoquinoline
(E)-6-Cyano-2-(4-(3-(5-indolyl)propenoyl)aminobutyl)-1,2,3,4-tetrahydroisoquinoline
(E)-6-Cyano-2-(4-(3-(5-benzimidazolyl)propenoyl) aminobutyl)-1,2,3,4-tetrahydroisoquinoline
(E)-6-Bromo-2-(4-(3-(2-naphthyl)propenoyl)aminobutyl)-1,2,3,4-tetrahydroisoquinoline
(E)-6-Bromo-2-(4-(3-(5-indolyl)propenoyl)aminobutyl)-1,2,3,4-tetrahydroisoquinoline
(E)-6-Bromo-2-(4-(3-(5-(2-methyl)indolylpropenoyl) amino)butyl)-1,2,3,4-tetrahydroisoquinoline
(E)-6-Bromo-2-(4-(3-(6-indolylpropenoyl)amino)butyl)-1,2,3,4-tetrahydroisoquinoline
(E)-6-Chloro-2-(4-(3-(5-indolylpropenoyl)amino)butyl)-1,2,3,4-tetrahydroisoquinoline
(E)-6-Chloro-2-(4-(3-(2-naphthylpropenoyl)amino)butyl)-1,2,3,4-tetrahydroisoquinoline
(E)-6-Bromo-2-(4-(3-(5-(3-methyl)indolylpropenoyl) amino)butyl)-1,2,3,4-tetrahydroisoquinoline
(E)-6-Chloro-2-(4-(3-(6-indolylpropenoyl)amino)butyl)-1,2,3,4-tetrahydroisoquinoline
(E)-2-($^4$-(3-(5-(3-Acetyl)indolyIpropenoyl)amino)butyl)-6-bromo-1,2,3,4-tetrahydroisoquinoline
(E)-$^6$-Bromo-2-(4-(3-(6-(2-methyl)indolylpropenoyl) amino)butyl)-1,2,3,4-tetrahydroisoquinoline
(E)-6-Bromo-2-(4-(3-(5-(2-methyl)-1H-benzimidazolylpropenoyl)amino)butyl)-1,2,3,4-tetrahydroisoquinoline
(E)-6-Bromo-2-(4-(3-(5-(1-methyl)indolylpropenoyl) amino)butyl)-1,2,3,4-tetrahydroisoquinoline
2-(4-(4-(4-Acetylphenyl)benzoylamino)butyl)-6-trifluoromethoxy-1,2,3,4-tetrahydroisoquinoline
6-Methoxy-2-(4-(4-phenylbenzoylamino)butyl)-1,2,3,4-tetrahydroisoquinoline
6-Hydroxy-2-(4-(4-phenylbenzoylamino)butyl)-1,2,3,4-tetrahydroisoquinoline
2-(4-(4-Phenylbenzoylamino)butyl)-6-trifluoromethylsulfonyloxy-1,2,3,4-tetrahydroisoquinoline and salts thereof.

The present invention also provides a process for preparing compounds of formula (I) which process comprises:

(a) reacting a compound of formula (II):

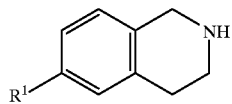

Formula (II)

wherein $R^1$ and q are as hereinbefore defined;

with a compound of formula (III):

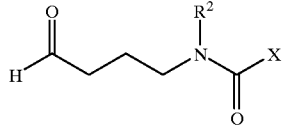

Formula (III)

wherein $R^2$ and X are as hereinbefore defined;

(b) reaction of a compound of formula (IV):

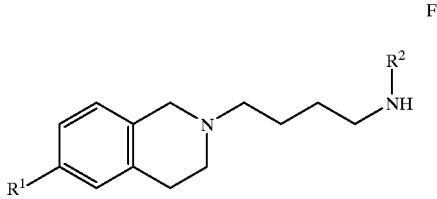

Formula (IV)

wherein $R^1$ and $R^2$ are as hereinbefore defined;

with a compound of formula (V):

XCOL     Formula (V)

wherein X is as hereinbefore defined and L is a halogen atom or the residue of an activated ester;

(c) to prepare a compound of formula (I) wherein $R^1$ is $Ar^3$—Z and Z is a bond, reacting a compound of formula (VI):

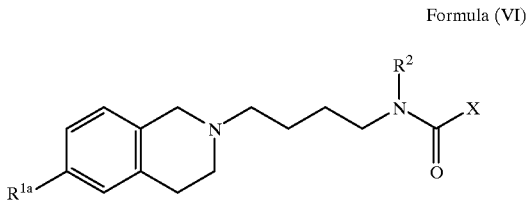

Formula (VI)

wherein $R^{1a}$ represents a group W wherein W is a halogen atom or a trifluoromethylsulphonyloxy group, or W is a group M selected from a boron derivative e.g. a boronic acid function $B(OH)_2$ or a metal function such as trialkylstannyl e.g. $SnBu_3$, zinc halide or magnesium halide; with a compound $Ar^3$—$W^1$, wherein $W^1$ is a halogen atom or a trifluoromethylsulphonyloxy group when W is a group M or $W^1$ is a group M when W is a halogen atom or a trifluoromethylsulphonyloxy group;

(d) to prepare a compound of formula (I) wherein $R^1$ is $Ar^3$—Z and Z is O or S, reacting a compound of formula (VII):

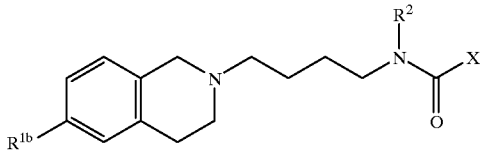

Formula (VII)

wherein $R^{1b}$ represents a group ZH; with a reagent serving to introduce the group $Ar^3$;

(e) to prepare a compound of formula (I) where X represents the group —Ar—Y—$Ar^1$ and Y is a bond, reaction of a compound of formula (VIII):

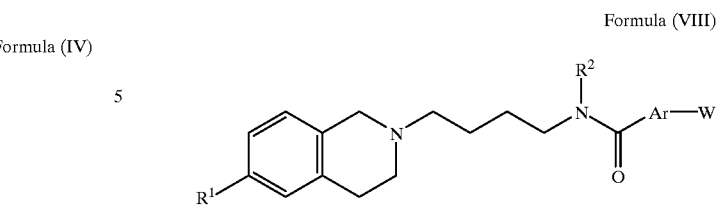

Formula (VIII)

wherein $R^1$, $R^2$, Ar and W are as hereinbefore defined, with a compound $Ar^1$—$W^1$, wherein $W^1$ is a halogen atom or a trifluoromethylsulphonyloxy group when W is a group M, or $W^1$ is a group M when W is a halogen atom or a trifluoromethylsulphonyloxy group.

(f) interconversion of one compound of formula (I) to a different compound of formula (I) e.g. (i) alkylation of a compound (I) wherein $R^2$ represents hydrogen, (ii) conversion of one $R^1$ from alkoxy (e.g.methoxy) to hydroxy, or (iii) conversion of $R^1$ from hydroxy to sulphonyloxy, eg alkylsulphonyloxy or trifluoromethanesulphonyloxy; (iv) conversion of a compound wherein Y represents S to a compound wherein Y is $SO_2$ or (v) conversion of Y from CO to $CH_2$; and optionally thereafter forming a salt of formula (I).

Process (a) requires the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol or dichloroethane.

Process (b) may be effected by methods well known in the art for formation of an amide bond.

Reaction of a compound of formula (VI) with $Ar^3W^1$, according to process (c) or a compound of formula (VIII) with $Ar^1$—$W^1$ according to process (e) may be effected in the presence of a transition metal eg palladium catalyst such as bis-triphenylphosphinepalladium dichloride or tetrakis-triphenylphosphinepalladium (0). When M represents a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulphonyloxy group such as trifluoromethylsulphonyloxy; and $W^1$ is preferably a group M, such as trialkylstannyl or $B(OH)_2$.

In process (d) the reagent serving to introduce the group $Ar^3$ is preferably a compound of formula $Ar^3$—Hal, wherein Hal is a halogen atom. The reaction may be effected in the presence of a base, such as potassium carbonate, in a solvent such as dimethylformamide.

Interconversion reactions according to process (f) may be effected using methods well known in the art.

Compounds of formula (II) may be prepared by methods known in the art.

Compounds of formula (III) are known or may be prepared using standard procedures.

A compound of formula (IV) may be prepared by alkylation of a compound of (II) by standard methods. Thus, for example a compound of formula (II) may be reacted with N-(4-bromobutylphthalimide) followed by removal of the phthalimide group to give a compound of formula (IV) where $R^2$ is hydrogen. Compounds where $R^2$ is alkyl may be prepared by subsequent reaction with the appropriate aldehyde using conditions analogous to process (a) above.

Compounds of formula (VI), (VII) or (VIII) may be prepared by processes analogous to (a) or (b) described above. Compounds $Ar^1W^1$, $Ar^3W^1$ and $Ar^3Hal$ are commercially available or may be prepared by standard methods.

Compounds of formula (I) have been found to exhibit affinity for dopamine receptors, in particular the $D_3$ receptor, and are expected to be useful in the treatment of disease states which require modulation of such receptors, such as psychotic conditions. Compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

We have found that certain compounds of formula (I) are dopamine $D_3$ receptor antagonists, others may be agonists and partial agonists. The functional activity of compounds of the invention (i.e. whether they are antagonists, agonists or partial agonists) can be readily determined using the test method described hereinafter, which does not require undue experimentation. $D_3$ antagonists are of potential use as antipsychotic agents for example in the treatment of schizophrenia, schizo-affective disorders, psychotic depression, mania, paranoid and delusional disorders. Conditions which may be treated by dopamine $D_3$ receptor agonists include dyskinetic disorders such as Parkinson's disease, neuroleptic-induced parkinsonism and tardive dyskinesias; depression; anxiety, memory disorders, sexual dysfunction and drug (eg. cocaine) dependency.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

A preferred use for $D_3$ agonists according to the present invention is in the treatment of dyskinetic disorders such as Parkinson's disease.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg,e .g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of [$^{125}$I] iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at $-40°$ C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM CaCl$_2$, 1 mM MgCl$_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 $\mu$M iodosulpride. For competition curves, 14 concentrations (half-log dilutions) of competing cold drug were used. Competition curves were analysed simultaneously whenever possible using non-linear least-squares fitting procedures, capable of fitting one, two or three site models.

Compounds of Examples tested according to this method had pKi values in the range 7.0–8.5 at the human cloned dopamine $D_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912) In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5%CO$_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Agonists and antagonists were diluted in running medium. In experiments to determine agonist activity, cells were exposed (4.5 min for hD2, 7.5 min for hD3) to increasing concentrations of putative agonist at half hour intervals. Seven concentrations of agonist were used. Peak acidification rate to each agonist concentration was determined and concentration-response curves fitted using Robofit [Tilford, N. S., Bowen, W. P. & Baxter, G. S. Br. J. Pharmacol. (1995) in press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Pharmaceutical Formulations

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension | |
|---|---|
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin The invention is further illustrated by the following non-limiting examples Description 1
(3-Trifluoromethoxy)phenylethylamine hydrochloride To a stirred solution of zirconium (IV) chloride (11.8 g, 49.5 mmol) in dry tetrahydrofuran (200 ml) at 20° C. under argon was added, portionwise, sodium borohydride (7.5 g, 0.197 mol). Mixture was stirred for 1 h, then 3-trifluoromethoxyphenylacetonitrile (4.2 g, 20.9 mmol) was added. Stirring was continued for 24 h, then water (10 ml) was added dropwise, keeping the internal temperature below 10° C. The mixture was partitioned between dilute aqueous ammonia (500 ml) and ethyl acetate (4×100 ml). Organic extracts were dried ($Na_2SO_4$) and evaporated in vacuo to give an oil which was treated with ethereal HCl to give the title compound (2.1 g, 50%).

Mass spectrum ($API^+$): Found 206 ($MH^+$). $C_9H_{10}F_3NO$ requires 205.

The following compounds were prepared in a similar manner to description 1.
(a) (3-Trifluoromethyl)phenethylamine hydrochloride
  Mass spectrum ($API^+$): Found 190 ($MH^+$). $C_9H_{10}F_3N$ requires 189.
(b) (3-Bromo)phenethylamine hydrochloride
  Mass spectrum ($API^+$): Found 200 ($MH^+$). $C_8H_{10}{}^{79}BrN$ requires 199.

Description 2
N-(2-(3-Trifluoromethoxyphenyl)ethyl)trifluoroacetamide

To a stirred mixture of (3-trifluoromethoxy) phenethylamine hydrochloride (5.85 g, 24.2 mmol) and 2,6-lutidine (5.65 ml; 5.19 g, 48.6 mmol) in dichloromethane (100 ml) at 0° C. under argon was added, dropwise, trifluoroacetic anhydride (3.42 ml, 5.08 g, 24.2 mmol). Resultant was stirred at 20° C. for 18 h then partitioned between water (100 ml) and dichloromethane (2×100 ml). Organic phase was washed with 1M hydrochloric acid (100 ml), saturated aqueous $NaHCO_3$ (100 ml), dried ($Na_2SO_4$) then evaporated in vacuo to give the title compound (6.14 g, 84%) as an oil.

Mass spectrum ($API^+$): Found 302 ($MH^+$). $C_{11}H_9F_6NO_2$ requires 301.

The following compounds were prepared in a similar manner to description 2.
(a) N-(2-(3-Trifluoromethylphenyl)ethyl)trifluoroacetamide
  Mass spectrum ($API^-$): Found 284 $(M-H)^-$. $C_{10}H_9F_6NO$ requires 285.
(b) N-(2-(3-Bromophenyl)ethyl)trifluoroacetamide
  Mass spectrum ($API^-$): Found 294 $(M-H)^-$. $C_{10}H_9{}^{79}BrF_3NO$ requires 295.

Description 3
6-Trifluoromethoxy-1,2,3,4-tetrahydroisoquinoline hydrochloride

N-(2-(3-Trifluoromethoxyphenyl)ethyl) trifluoroacetamide (6.144 g, 19.6 mmol) was treated in a manner similar to that described in G. E. Stokker, Tetrahedron Letters 37 5453 1996. The resulting product (6.13 g) was treated with anhydrous potassium carbonate (15.0 g, 0.108 mol) in methanol (140 ml) containing water (22 ml) at reflux for 2 h. The mixture was cooled, evaporated in vacuo, then partitioned between water (200 ml) and dichloromethane (4×50 ml). Combined organic extracts were dried ($Na_2SO_4$) and evaporated in vacuo to give an oil (4.14 g), which was treated with ethereal HCl. Recrystallisation of the resulting solid from ethanol gave the title compound (2.33 g, 45%) as a colourless solid.

$^1$H NMR (DMSO-$d_6$)δ: 3.07 (2H, t, J=7 Hz), 3.39 (2H, t, J=7 Hz), 4.29 (2H, s). 7.27 (1H, d, J=9 Hz), 7.32 (1H, s), 7.40 (1H, d, J=9 Hz), 9.81 (2H, br s).

Mass spectrum ($API^+$): Found 218 ($MH^+$). $C_{10}H_{10}F_3NO$ requires 217.

The following compounds were prepared in a similar manner to description 3.
(a) 6-Trifluoromethyl-1,2,3,4-tetrahydroisoquinoline hydrochloride
  Mass spectrum ($API^+$): Found 202 ($MH^+$). $C_{10}H_{10}F_3N$ requires 201.
(b) 6-Bromo-1,2,3,4-tetrahydroisoquinoline hydrochloride
  $^1$H NMR (DMSO-$d_6$)δ: 3.08 (2H, t, J=7 Hz), 3.35 (2H, t, J=7 Hz), 4.23 (2H, s), 7.15 (1H, d, J=9 Hz), 7.36 (1H, d, J=9 Hz), 7.39 (1H, s).

Description 4
6-Cyano-1,2,3,4-tetrahydroisoquinoline hydrochloride

A solution of 6-bromo-1,2,3,4-tetrahydroisoquinoline hydrochloride (6.0 g, 24 mmol) and triethylamine (7.4 ml, 5.36 g, 53 mmol) in dichloromethane (100 ml) was treated with trifluoroacetic anhydride (3.7 ml, 5.54 g, 26.4 mmol) with ice cooling. Mixture was stirred at 20° C. for 1.5 h. then partitioned between saturated aqueous $NaHCO_3$ (250 ml) and dichloromethane (3×50 ml). Combined organic extracts were dried ($Na_2SO_4$) and evaporated in vacuo to give a solid (8.3 g). A mixture of the latter with copper (I) cyanide (5.1 g, 56.6 mmol) in 1-methyl-2-pyrrolidinone (100 ml) was heated at reflux under argon for 4 h, then cooled and partitioned between water (300 ml), 0.880 aqueous ammonia (100 ml) and dichloromethane (5×200 ml). Combined organic extracts were dried ($Na_2SO_4$) and evaporated in vacuo to give an oil. The latter was dissolved in ether and treated with ethereal HCl to give the title compound (4.47 g, 85%) as a colourless solid.

Mass spectrum (API$^+$): Found 159 (MH$^+$). $C_{10}H_{10}N_2$ requires 158.

Description 5
(4-Trifluoroacetamido)butyraldehyde

To a solution of 4-aminobutyraldehyde diethyl acetal (16.10 g, 0.10 mmol) and triethylamine (18.06 ml, 0.12 mol) in dichloromethane (150 ml) at 0° C. was added a solution of trifluoroacetic anhydride (16.9 ml, 0.11 mol) in dichloromethane (60 ml). The reaction mixture was warmed to room temperature and stirred for 3 h, then partitioned between 5% aq NaHCO$_3$ (400 ml) and dichloromethane (400 ml). The aqueous layer was extracted further with dichloromethane (3×100 ml), the combined extracts were dried (Na$_2$SO$_4$) and evaporated in vacuo to afford a pale yellow oil which was added to a stirred mixture of THF (300 ml) and water (500 ml). 5N Sulfuric acid (2.27 ml) was added and the reaction mixture left to stir at room temperature for 18 h. Saturated aqueous sodium bicarbonate (500 ml) was added and the product was extracted into dichloromethane (4×100 ml). The combined organic extracts were dried (Na$_2$SO$_4$) and evaporated in vacuo to afford the title compound as a yellow oil (15.42 g, 65%).

$^1$H NMR (CDCl$_3$)δ: 1.95 (2H, m), 2.62 (2H, t, J=8 Hz), 3.38 (2H, m), 7.54–7.80 (1H, br s), 9.77 (1H, s).

Description 6
2-(4-Trifuoroacetamido)butyl-6-trifuoromethoxy1,2,3,4-tetrahydroisoquinoline A mixture of 6-trifluoromethoxy-1,2,3,4-tetrahydroisoquinoline (1.98 g, 9.1 mmol), (4-trifluoroacetamido)butyraldehyde (1.67 g, 9.1 mmol), and sodium triacetoxyborohydride (2.87 g, 13.7 mmol) in dichloroethane (40 ml) was stirred at 20° C. for 18 h. Resultant was partitioned between saturated aqueous NaHCO, (200 ml) and dichloromethane (3×50 ml). Combined organic extracts were dried (Na$_2$SO$_4$) and evaporated in vacuo to give an oil (3.6 g). Chromatoorphy on silica eluting with 30–100% ethyl acetate-hexane gave the title compound (2.97 g, 85%) as an oil.

Mass spectrum (API$^+$): Found 385 (MH$^+$). $C_{16}H_{18}F_6N_2O_2$ requires 384.

The following compounds were prepared in a similar manner to description 6.

(a) 2-(4-Trifluoroacetamido)butyl-6-trifluoromethyl-1,2,3,4-tetrahydroisoquinoline Mass spectrum (API$^+$): Found 369 (MH$^+$). $C_{16}H_{18}F_6N_2O$ requires 368.

(b) 6-Cyano-2-(4-trifluoroacetamido)butyl-1,2,3,4-tetrahydroisoquinoline

Mass spectrum (API$^+$): Found 326 (MH$^+$). $C_{16}H_{18}F_3N_3O$ requires 325.

(c) 6-Bromo-2-(4-trifluoroacetamido)butyl-1,2,3,4-tetrahydroisoquinoline

Mass spectrum (API$^+$): Found 379 (MH$^+$). $C_{15}H_{18}{}^{79}BrF_3N_2O$ requires 378.

Description 7
2-(4-Aminobutyl)-6-trifluoromethoxy-1,2,3,4-tetrahydroisoquinoline A mixture of 2-(4-trifluoroacetamido)butyl-6-trifluoromethoxy-1,2,3,4-tetrahydroisoquinoline (2.94 g, 7.7 mmol), anhydrous potassium carbonate (5.6 g, 40.5 mmol), water (11 ml) and methanol (70 ml) was heated at reflux for 2 h, cooled, then evaporated in vacuo. Residue was partitioned between water (50 ml) and dichloromethane (4×50 ml) and the combined extracts were dried (Na$_2$SO$_4$) then evaporated in vacuo to give the title compound (2.14 g, 97%) as an oil.

Mass spectrum (API$^+$): Found 289 (MH$^+$). $C_{14}H_{19}F_3N_2O$ requires 288.

The following compounds were prepared using a method similar to description 7.

(a) 2-(4-Aminobutyl)-6-trifluoromethyl-1,2,3,4-tetrahydroisoquinoline

Mass spectrum (API$^+$): Found 273 (MH$^+$). $C_{14}H_{19}F_3N_2$ requires 272.

(b) 2-(4-Aminobutyl)-6-cyano-1,2,3,4-tetrahydroisoquinoline

Mass spectrum (API$^+$): Found 230 (MH$^+$). $C_{14}H_{19}N_3$ requires 229.

(c) 2-(4-Aminobutyl)-6-bromo-1,2,3,4-tetrahydroisoquinoline

Mass spectrum (API$^+$): Found 283 (MH$^+$). $C_{13}H_{19}{}^{79}BrN_2$ requires 282.

Description 8
N-(4-Hydroxybutyl)-4-phenylbenzamide

To a stirred solution of 4-amino-1-butanol (7.34 g, 82 mmol) and triethylamine (12.3 ml; 8.82 g, 87 mmol) in dichloromethane (100 ml) at 0° C. was added a solution of 4-phenylbenzoyl chloride (18.36 g, 85 mmol) in dichloromethane (800 ml) dropwise over 1.2 h. Resultant was stirred at 0° C. for 2 h then at room temperature for 18 h. The resulting white solid was filtered off (15.94 g) and the filtrate washed with 5% aqueous sodium hydroxide (1L). The organic phase was dried (Na$_2$SO$_4$) and evaporated in vacuo to give a white solid (4.96 g) which was combined with the above to give the title compound (20.9 g, 93%).

$^1$H NMR (DMSO-d$_6$)δ: 1.4–1.7 (4H, m), 3.26 (2H, q, J=7 Hz), 3.42 (2H, q, J=7 Hz), 4.43 (1H, t, J=6 Hz), 7.35–7.55 (3H, m), 7.75 (4H, m), 7.94 (2H, d, J=9 Hz), 8.52 (1H, t, J=7 Hz).

Description 9
4-(4-Phenylbenzoylamino)butyraldehyde

To a mechanically-stirred solution of N-(4-hydroxybutyl)-4-phenylbenzamide (11.2 g, 44.2 mmol) and triethylamine (148 ml; 107.5 g, 1.06 mol) in dimethyl sulfoxide (250 ml) at room temperature was added, dropwise over 1h, a solution of pyridine-sulfur trioxide complex (43.7 g, 0.273 mol) in dimethyl sulfoxide (200 ml) with external cooling using a cold water bath. The mixture was stirred at room temperature for 3 h, then 2M hydrochloric acid (550 ml) was added slowly with ice cooling. Resultant was diluted with water (1L) then extracted with ethyl acetate (3×500 ml). The combined extracts were washed with 2M hydrochloric acid (3×500 ml) and water (3×500 ml) then dried (Na$_2$SO$_4$) and evaporated in vacuo to give a semi solid (12 g). Chromatography on silica gel eluting with 10–100% ethyl acetate-hexane gave the title compound as a white solid (4.72 g, 42%).

$^1$H NMR (CDCl$_3$)δ: 2.00 (2H, m), 2.65 (2H, m), 3.52 (2H, q, J=8 Hz), 6.54 (1H, br m), 7.35–7.53 (3H, m), 7.54–7.71 (4H, m), 7.85 (2H, m), 9.83 (1H, s).

Description 10
6-Chloro-1,2,3,4-tetrahydroisoquinoline

A mixture of 4-chlorobenzaldehyde (22.47 g, 0.16 mol) and ethanolamine (58.5 g, 58.5 ml, 0.96 mol) in methanol (320 ml) and glacial acetic acid (60 ml) was treated portionwise with sodium cyanoborohydride (6.05 g, 0.096 mol). The mixture was stirred at room temperature, under an atmosphere of argon for 18 h, and then evaporated in vacuo. The residues were dissolved in water (300 ml), and acidified to pH4 using 5N HCl. The aqueous phase was washed with ether and then basified to pH11 using 10N NaOH and extracted into ether (2×200 ml). The combined organic layers were dried over Na$_2$SO$_4$ and evaporated in vacuo to give a yellow oil, which was dissolved in ether and treated with 1M HCl in ether (1.1 eq) and dried to give a white solid (27.47 g).

The amine hydrochloride (20.15 g, 91 mmol), ammonium chloride (3.51 g, 66 mmol) and aluminium chloride (23.4 g, 175 mmol) in a flask fitted with an overhead stirrer was immersed in an oil bath at 185° C. Further portions of aluminum chloride were added at 30 mins (11.8 g, 88 mmol), 70 mins (23.6 g, 177 mmol), 17 hours (20 g, 150 mmol), and 40 hours (20 g, 150 mmol). The reaction mixture was cooled in an ice/methanol bath, and ice added cautiously (300 ml), and then acidified using 5N HCl (50 ml). The mixture was diluted with water (300 ml), and further acidified using 5N HCl (150 ml), and then basified with 50% NaOH (pH10). The mixture was extracted with ether (3×200 ml), and the combined organic extracts were dried over $Na_2SO_4$ and evaporated in vacuo to give an oil (9.32 g) which was purified by distillation to give a brown liquid (4.0 g, 26%).

Mass spectrum ($API^+$): Found 168 ($MH^+$). $C_9H_{10}{}^{35}ClN$ requires 167.

EXAMPLE 1

(E)-2-(4-(3-(2-Naphthyl)propenoyl)aminobutyl)-6-trifluoromethoxy-1,2,3,4-tetrahydroisoquinoline A mixture of 2-(4-aminobutyl)-6-trilluoromethoxy-1,2,3,4-tetrahydroisoquinoline (0.30 g, 1.04 mmol), 1-ethyl-3-(3-dimethylaminopropyl)carbodiimide hydrochloride (0.199 g, 1.04 mmol), (E)-3-(2-naphthyl)propenoic acid (0.206 g, 1.04 mmol) and 1-hydroxybenzotriazole (0.02 g) in dichloromethane was shaken at 20° C. for 18 h, then treated with saturated aqueous $NaHCO_3$. Shaking was continued for 0.2 h, then the organic phase was separated. Chromatography of the organic phase on silica using 10–100% ethyl acetate-hexane gradient elution gave the title compound (0.266 g, 55%) as a colourless solid. Mass specwrum ($API^+$): Found 469 ($MH^+$). $C_{27}H_{27}F_3N_2O_2$ requires 468.

$^1$H NMR ($CDCl_3$)δ: 1.75 (4H, m), 2.59 (2H, m), 2.76 (2H, t, J=7 Hz), 2.95 (2H, t, J=7 Hz), 3.45 (2H, m), 3.66 (2H, s), 6.25 (1H, d, J=16 Hz), 7.00 (3H, m), 7.34 (1H, d, J=9 Hz), 7.48 (2H, m), 7.60–7.87 (6H, m).

The following compounds were prepared in a similar manner to Example 1

(a) (E)-2-(4-(3-(5-Indolyl)propenoyl)aminobutyl)-6-trfluoromethoxy-1,2,3,4-tetrahydroisoquinoline Mass spectrum ($API^+$): Found 458 ($MH^+$). $C_{25}H_{26}F_3N_3O_2$ requires 457.

$^1$H NMR ($CDCl_3$)δ: 1.70 (4H, m), 2.54 (2H, m), 2.73 (2H, t, J=7 Hz), 2.94 (2H, t, J=7 Hz), 3.43 (2H, m), 3.62 (2H, s), 6.15 (1H, d, J=16 Hz), 6.54 (1H, m), 6.84 (1H, m), 7.00 (3H, m), 7.17 (2H, m), 7.26 (1H, d, J=9 Hz), 7.61 (1H, s), 7.20 (1H, d, J=16 Hz), 8.78 (1H, br s).

(b) (E)-2-(4-(3-(5-Benzimidazolyl)propenoyl)aminobutyl)-6-trifluoromethoxy-1,2,3,4-tetrahydroisoquinoline Mass spectrum ($API^+$): Found 459 ($MH^+$). $C_{24}H_{25}F_3N_4O_2$ requires 458.

$^1$H NMR ($CDCl_3$)δ: 1.72 (4H, m), 2.59 (2H, m), 2.77 (2H, m), 2.95 (2H, m), 3.45 (2H, m), 3.66 (2H, s), 6.16 (1H, d, J=16 Hz), 7.03 (3H, m), 7.23 (3H, m), 7.58 (2H, m), 7.69 (1H, d, J=16 Hz), 8.05 (1H, s).

(c) (E)-2-(4-(3-(5-Indolyl )propenoyl)aminobutyl)-6-trifluoromethyl-1,2,3,4-tetrahydroisoquinoline Mass spectrum ($API^+$): Found 442 ($MH^+$). $C_{25}H_{26}F_3N_3O$ requires 441.

$^1$H NMR ($CDCl_3$)δ: 1.73 (4H, m), 2.59 (2H, m), 2.77 (2H, m), 2.99 (2H, m), 3.45 (2H, m), 3.70 (2H, s), 6.13 (1H, d, J=15 Hz), 6.56 (1H, m), 6.66 (1H, m), 7.15 (1H, d, J=8 Hz), 7.26 (3H, m), 7.39 (2H, m), 7.70 (2H, m), 8.26 (1H, m).

(d) (E)-6-Cyano-2-(4-(3-(5-indolyl)propenoyl)aminobutyl)-1,2,3,4-tetrahydroisoquinoline Mass spectrum ($API^+$): Found 399 ($MH^+$). $C_{25}H_{26}N_4O$ requires 398.

$^1$H NMR ($CDCl_3+CD_3OD$)δ 8 1.66 (4H, m), 2.55 (2H, m), 2.78 (2H, t, J=7 Hz), 2.95 (2H, t, J=7 Hz), 3.36 (2H, m), 3.66 (2H, s), 5.80 (1H, d, J=16 Hz), 6.50 (1H, d, J=3 Hz), 7.14 (1H, d, J=9 Hz), 7.23 (2H, m), 7.49 (3H, m), 7.67 (1H, d, J=16 Hz), 7.71 (1H, s).

(e) (E)-6-Cyano-2-(4-(3-(5-benzimidazolyl)propenoyl)aminobutyl)-1,2,3,4-tetrahydroisoquinoline Mass spectrum ($API^+$): Found 400 ($MH^+$). $C_{24}H_{25}N_5O$ requires 399.

$^1$H NMR ($CDCl_3+CD_3OD$)δ: 1.75 (4H, m), 2.65 (2H, m), 2.92 (2H, m), 3.07 (2H, m), 3.48 (2H, m), 3.80 (2H, s), 6.04 (1H, d, J=16 Hz), 7.26 (1H, d, J=9 Hz), 7.49 (3H, m), 7.70 (1H, m), 7.78 (1H, d, J=16 Hz), 7.85 (1H, m), 8.16 (1H, s).

(f) (E)-6-Bromo-2-(4-(3-(2-naphthyl)propenoyl)aminobutyl)-1,2,3,4-tetrahydroisoquinoline Mass spectrum ($API^+$): Found 463 ($MH^+$). $C_{26}H_{27}{}^{79}BrN_2O$ requires 462.

$^1$H NMR ($CDCl_3$)δ: 1.73 (4H, m), 2.63 (2H, m), 2.78 (2H, t, J=7 Hz), 2.95 (2H, t, J=7 Hz), 3.44 (2H, m), 3.63 (2H, s), 6.17 (1H, d, J=16 Hz), 6.94 (1H, d, J=9 Hz), 7.26 (3H, m), 7.39 (1H, m), 7.47 (2H, m), 7.72 (1H, d, J=16 Hz), 7.79 (4H, m).

(g) (E)-6-Bromo-2-(4-(3-(5-indolyl)propenoyl)aminobutyl)-1,2,3,4-tetrahydroisoquinoline Mass spectrum ($API^+$): Found 452 ($MH^+$). $C_{24}H_{26}{}^{79}BrN_3O$ requires 451.

$^1$H NMR ($CDCl_3+CD_3OD$)δ: 1.65 (4H, m), 2.52 (2H, m), 2.71 (2H, m), 2.88 (2H, m), 3.37 (2H, m), 3.56 (2H, s), 6.18 (1H, d, J=16 Hz), 6.55 (1H, m), 6.91 (1H, d, J=9 Hz), 7.11–7.38 (5H, m), 7.66 (2H, m).

(h) (E)-6-Bromo-2-(4-(3-(5-(2-methyl)indolylpropenoyl)amino)butyl)-1,2,3,4-tetrahydroisoquinoline Mass spectrum ($API^+$): Found 468 ($MH^+$). $C_{25}H_{28}{}^{81}BrN_3O$ requires 467.

NMR ($DMSO-d_6$)δ: 1.58 (4H, m), 2.43 (3H, s), 2.51 (2H, t, J=6 Hz), 2.67 (2H, t, J=6 Hz), 2.86 (2H, t, J=6 Hz), 3.25 (2H, m), 3.55 (2H, s), 6.21 (1H, s), 6.53 (1H, d, J=16 Hz), 7.08 (1H, d, J=8 Hz), 7.32 (4H, m), 7.52 (1H, d, J=16 Hz), 7.61 (1H, m), 8.05 (1H, t, J=5 Hz), 11.15 (1H, s).

(i) (E)-6-Bromo-2-(4-(3-(6-indolylpropenoyl)amino)butyl)-1,2,3,4-tetrahydroisoquinoline Mass spectrum ($API^+$): Found 454 ($MH^+$). $C_{24}H_{26}{}^{81}BrN_3O$ requires 453.

$^1$H NMR ($CDCl_3$)δ: 1.71 (2H, m), 1.86 (2H, m), 2.57 (2H, m), 2.75 (2H, t, J=6 Hz), 2.95 (2H, m), 3.42 (2H, m), 3.61 (2H, s), 6.19 (2H, d, J=16 Hz), 6.54 (1H, d, J=3 Hz), 6.91 (1H, d, J=8 Hz), 7.07 (1H, dd, J=8, 2 Hz), 7.27 (4H, m), 7.37 (1H, s), 7.59 (1H, d, J=8 Hz), 7.68 (1H, d, J=16 Hz), 9.00 (1H, br s).

(j) (E)-6-Chloro-2-(4-(3-(5-indolylpropenoyl)amino)butyl)-1,2,3,4-tetrahydroisoquinoline Mass spectrum ($API^+$): Found 408 ($MH^+$). $C_{24}H_{26}{}^{35}ClN_3O$ requires 407.

$^1$H NMR ($CDCl_3$)δ: 1.71 (4H, m), 2.57 (2H, m), 2.74 (2H, m), 2.93 (2H, m), 3.41 (2H, m), 3.62 (2H, s), 6.06 (1H, d, J=16 Hz), 6.57 (1H, br s), 6.97 (1H, m), 7.06 (4H, m), 7.22 (1H, m), 7.34 (1H, d, J=8 Hz), 7.62 (1H, s), 7.68 (1H, d, J=16 Hz), 8.33 (1H, br, s).

(k) (E)-6-Chloro-2-(4-(3-(2-naphthylpropenoyl)amino)butyl)-1,2,3,4-tetrahydroisoquinoline Mass spectrum ($API^+$): Found 419 ($MH^+$). $C_{26}H_{27}{}^{35}ClN_2O$ requires 418.

$^1$H NMR ($CDCl_3$)δ: 1.73 (4H, m), 2.58 (2H, m), 2.75 (2H, m), 2.94 (2H, m), 3.43 92H, m), 3.64 (2H, s), 6.16 (1H, d, J=16 Hz), 6.99 (1H, m), 7.14 (2H, m), 7.20 (2H, m), 7.39 (1H, m), 7.49 (2H, m), 7.78 (4H, m).

(l) (E)-6-Bromo-2-(4-(3-(5-(3-methyl )indolylpropenoyl) amino)butyl)-1,2,3,4-tetrahydroisoquinoline Mass spectrum (API$^+$): Found 468 (MH$^+$). $C_{25}H_{28}{}^{81}BrN_3O$ requires 467.

$^1$H NMR (CDCl$_3$)δ: 1.71 (4H, m), 2.32 (3H, s), 2.56 (2H, m), 2.72 (2H, t, J=6 Hz), 2.92 (2H, m), 3.43 (2H, m), 3.59 (2H, s), 6.12 (1H, d, J=16 Hz), 6.86 (1H, br s), 6.91 (1H, d, J=9 Hz), 6.97 (1H, s), 7.07 (1H, d, J=8 Hz), 7.25–7.30 (3H, m), 7.62 (1H, s), 7.72 (1H, d, J=16 Hz), 8.14 (1H, brs).

(m) (E)-6-Chloro-2-(4-(3-(6-indolylpropenoyl)amino) butyl)-1,2,3,4-tetrahydroisoquinoline Mass spectrum (API$^+$): Found 408 (MH$^+$). $C_{24}H_{26}{}^{35}ClN_3O$ requires 407.

$^1$H NMR (CDCl$_3$)δ: 1.73 (4H, m), 2.57 (2H, mn), 2.74 (2H, m), 2.94 (2H, m), 3.41 (2H, m), 3.63 (2H, s), 6.05 (1H, d, J=16 Hz), 6.54 (1H, m), 7.00 (2H, m), 7.14 (2H, m) 7.27 (3H, m), 7.57 (1H, m), 7.67 (1H, d, J=16 Hz), 8.42 (1H, m).

(n) (E)-2-(4-(3-(5-(3-Acetyl)indolylpropenoyl)amino) butyl)-6-bromo-1,2,3,4-tetrahydroisoquinoline Mass spectrum (API$^+$): Found 496 (MH$^+$). $C_{26}H_{28}{}^{81}BrN_3O_2$ requires 495.

$^1$H NMR (DMSO-d$_6$)δ: 1.56 (4H, m), 2.50 (5H, m), 2.63 (2H, m), 2.82 (2H, m), 3.23 (2H, m), 3.53 (2H, s), 6.68 (1H, d, J=16 Hz), 7.05 (1H, d, J=8 Hz), 7.30 (2H, m), 7.41 (1H, m), 7.51 (1H, s), 7.56 (1H, m), 8.16 (1H, m), 8.40 (2H, m), 12.10 (1H, s).

(o) (E)-6-Bromo-2-(4-(3-(6-(2-methyl )indolylpropenoyl) amino)butyl)-1,2,3,4-tetrahydroisoquinoline Mass spectrum (API$^+$): Found 468 (MH$^+$). $C_{25}H_{28}{}^{81}BrN_3O$ requires 467.

$^1$H NMR (DMSO-d$_6$)δ: 1.50 (4H, m), 2.35 (3H, s), 2.40 (2H, m), 2.60 (2H, t, J=6 Hz), 2.76 (2H, t, J=6 Hz), 3.16 (2H, m), 3.45 (2H, s), 6.10 (1H, s), 6.47 (1H, d, J=16 Hz), 6.98 (1H, d, J=8 Hz), 7.10 (1H, m), 7.25 (2H, m), 7.35 (2H, m), 7.42 (1H, d, J=16 Hz), 7.95 (1H, t, J=5 Hz), 11.06 (1H, s).

(p) (E)-6-Bromo-2-(4-(3-(5-(2-rnethyl)-1H-benzimidazolylpropenoyl)amino)butyl)-1,2,3,4-tetrahydroisoquinoline Mass spectrum (API$^+$): Found 469 (MH$^+$). $C_{24}H_{27}{}^{81}BrN_4O$ requires 468.

$^1$H NMR (DMSO-d$_6$)δ: 1.60 (4H, m), 2.60 (2H, m), 2.64 (3H, s), 2.75 (2H, t, J=6 Hz), 2.90 (2H, t, J=6 Hz), 3.30 (2H, m), 3.60 (2H, s), 6.65 (1H, d, J=16 Hz), 7.15 (1H, d, J=8 Hz), 7.45 (3H, m), 7.65 (3H, m), 8.20 (1H, m), 12.50 (1H, s).

(q) (E)-6-Bromo-2-(4-(3-(5-(1-methyl)i ndolylpropenoyl) amino)butyl)-1,2,3,4-tetrahydroisoquinoline Mass spectrum (API$^+$): Found 468 (MH$^+$). $C_{25}H_{28}{}^{81}BrN_3O$ requires 467.

$^1$H NMR (CDCl$_3$)δ: 1.69 (4H, m), 2.56 (2H, t, J=6 Hz), 2.72 (2H, t, J=6 Hz), 2.90 (2H, m), 3.38 (2H, m), 3.58 (2H, s), 3.81 (3H, s), 6.27 (1H, d, J=16 Hz), 6.48 (1H, d, J=3 Hz), 6.93 (1H, d, J=9 Hz), 7.08 (1H, d, J=3 Hz), 7.20–7.30 (4H, m), 7.45 (1H, br s), 7.63 (1H, s), 7.65 (1H, d, J=16 Hz).

(r) 2-(4-(4-(4-Acetylphenyl)benzoylamnino)butyl)-6-trifluoromethoxy-1,2,3,4-tetrahydroisoquinoline Mass spectrum (API$^+$): Found 511 (MH$^+$). $C_{29}H_{29}F_3N_2O_3$ requires 510.

$^1$H NMR (CDCl$_3$)δ: 1.75 (4H, m), 2.60 (2H, m), 2.66 (3H, s), 2.75 (2H, t, J=6 Hz), 2.93 (2H, t, J=6 Hz), 3.52 (2H, m), 3.60 (2H, s), 6.98 (3H, m), 7.38 (1H, m), 7.45 (2H, d, J=8 Hz), 7.65 (2H, d, J=8 Hz), 7.74 (2H, d, J=8 Hz), 8.03 (2H, d, J=8 Hz).

EXAMPLE 2

6-Methoxy-2-(4-(4-phenylbenzoylamino)butyl)-1,2,3,4-tetrahydroisoquinoline

A mixture of 6-methoxy-1,2,3,4-tetrahydroisoquinoline (1.00 g, 6.2 mmol), 4-(4-phenylbenzoylamino) butyraldehyde (1.64 g, 6.2 mmol), sodium triacetoxyborohydride (1.94 g, 9.2 mmol) and dichloromethane (50 ml) was stirred at 20° C. for 18 h. Resulting solution was partitioned between saturated aqueous NAHCO$_3$ (50 ml) and dichloromethane (3×50 ml). Combined organic extracts were dried (Na$_2$SO$_4$) and evaporated in vacuo to give a solid. Trituration with 1:1 dichloromethane-ether gave the title compound (0.80 g, 32%).

Mass spectrum (API$^+$): Found 415 (MH$^+$). $C_{27}H_{30}N_2O_2$ requires 414.

$^1$H NMR (CDCl$_3$)δ: 1.78 (4H, m), 2.59 (2H, m), 2.72 (2H, t, J=6 Hz), 2.87 (2H, t, J=6 Hz), 3.51 (2H, m), 3.55 (2H, s), 3.74 (3H, s), 6.61 (1H, dd, J=2 Hz), 6.70 (1H, dd, J=9, 2 Hz), 6.90 (1H, d, J=9 Hz), 7.30–7.50 (5H, m), 7.55 (2H, m), 7.68 (3H, m).

EXAMPLE 3

6-Hydroxy-2-(4-(4-phenylbenzoylamino)butyl)-1,2,3,4-tetrahydroisoquinoline

A mixture of 6-methoxy-2-(4-(4-phenylbenzoylamino) butyl)-1,2,3,4-tetrahydroisoquinoline (1.18 g, 2.8 mmol) and dichloromethane (50 ml) was treated dropwise with a solution of boron tribromide in dichloromethane (1M; 8.4 ml). The mixture was stirred at 20° C. for 18 h, then poured into a mixture of ice (100 g) and 0.880 ammonia (100 ml). Resulting mixture was extracted with dichloromethane (3×50 ml) and the combined extracts were dried (Na$_2$SO$_4$) and evaporated in vacuo. The residue was triturated with ether to give the title compound (0.86 g, 77%) as a yellow solid.

Mass spectrum (API$^+$): Found 401 (MH$^+$). $C_{26}H_{28}N_2O_2$ requires 400.

$^1$H NMR (CDCl$_3$)δ: 1.74 (4H, m), 2.54 (2H, m), 2.63–2.80 (4H, m), 3.50 (5H, m), 6.50 (1H, d, J=2 Hz), 6.63 (1H, dd, J=9, 2 Hz), 6.80 (1H, d, J=9 Hz), 7.30–7.66 (8H, m), 7.70 (2H, d, J=9 Hz).

EXAMPLE 4

2-(4-(4-Phenylbenzoylamino)butyl)-6-trifluoromethylsulfonyloxy-1,2,3,4-tetrahydroisoquinoline A mixture of 6-hydroxy-2-(4-(4-phenylbenzoylamino) butyl-1,2,3,4-tetrahydroisoquinoline (0.41 g, 1.0 mmol), triethylamine (0.14 ml; 1.0 mmol) and N-phenyltrifluoromethylsulfonimide (0.43 g, 1.2 mmol) in dichloromethane (15 ml) was stirred at 20° C. for 18 h. The resulting solution was washed with water (2×10 ml) and brine (20 ml), then dried (Na$_2$SO$_4$) and evaporated in vacuo to give an oil. Chromatography on silica with 20–80% ethyl acetate-pentane gradient elusion gave the title compound (0.22 g, 42%) as a solid.

Mass spectrum (API$^+$): Found 533 (MH$^+$). $C_{27}H_{27}F_3N_2O_4S$ requires 532.

$^1$H NMR (CDCl$_3$)δ: 1.75 (4H, m), 2.61 (2H, m), 2.75 (2H, t, J=6 Hz), 2.94 (2H, t, J=6 Hz), 3.53 (2H, m), 3.63 (2H, s), 7.00 (4H, m), 7.32–7.63 (7H, m), 7.74 (2H, d, J=9 Hz).

What is claimed is:

1. A compound of formula (I):

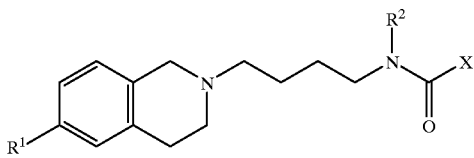

Formula (I)

wherein:

R¹ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulphonyl, $C_{1-4}$alkylsulphonyloxy, $C_{1-4}$alkylsulphonyl$C_{1-4}$alkyl, arylsulphonyl, arylsulphonyloxy, arylsulphonyl$C_{1-4}$alkyl, $C_{1-4}$alkylsulphonamido, $C_{1-4}$alkylamido, $C_{1-4}$alkylsulphonamido$C_{1-4}$alkyl, $C_{1-4}$alkylamido$C_{1-4}$alkyl, arylsulphonamido, arylcarboxamido, arylsulphonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of R³ and R⁴ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group Ar³—Z, wherein Ar³ represents an optionally substituted phenyl ring or an optionally substituted 5- or 6-membered aromatic heterocyclic ring and Z represents a bond, O, S, or $CH_2$;

R² represents a hydrogen atom or a $C_{1-4}$alkyl group;

X represents a group of the formula (a) or (b):

—Ar—Y—Ar¹ (a)

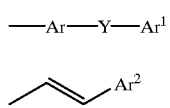 (b)

wherein

Ar and Ar¹ each independently represent an optionally substituted phenyl ring or an optionally substituted 5- or 6-membered aromatic heterocyclic ring; and Y represents a bond, —NHCO—, —CONH—, —CH₂—, or —(CH₂)ₘY¹(CH₂)ₙ—, wherein Y¹ represents O, S, SO₂, or CO and m and n each represent zero or 1 such that the sum of m+n is zero or 1;

Ar² represents an optionally substituted phenyl ring or an optionally substituted 5- or 6-membered aromatic heterocyclic ring; or an optionally substituted bicyclic ring system;

or a salt thereof.

2. A compound according to claim 1 wherein q represents 1.

3. A compound of formula (I) which is:

(E)-2-(4-(3-(2-Naphthyl)propenoyl)aminobutyl)-6-trifluoromethoxy-1,2,3,4-tetrahydroisoquinoline;

(E)-2-(4-(3-(5-Indolyl)propenoyl)aminobutyl)-6-trifluoromethoxy-1,2,3,4-tetrahydroisoquinoline;

(E)-2-(4-(3-(5-Benzimidazolyl)propenoyl)aminobutyl)-6-trifluoromethoxy-1,2,3,4-tetrahydroisoquinoline;

(E)-2-(4-(3-(5-Indolyl)propenoyl)aminobutyl)-6-trifluoromethyl-1,2,3,4-tetrahydroisoquinoline;

(E)-6-Cyano-2-(4-(3-(5-indolyl)propenoyl)aminobutyl)-1,2,3,4-tetrahydroisoquinoline;

(E)-6-Cyano-2-(4-(3-(5-benzimidazolyl)propenoyl) aminobutyl)-1,2,3,4-tetrahydroisoquinoline;

(E)-6-Bromo-2-(4-(3-(2-naphthyl)propenoyl)aminobutyl)-1,2,3,4-tetrahydroisoquinoline;

(E)-6-Bromo-2-(4-(3-(5-indolyl)propenoyl)(aminobutyl)-1,2,3,4-tetrahydroisoquinoline;

(E)-6-Bromo-2-(4-(3-(5-(2-methyl)indolylpropenoyl) amino)butyl)-1,2,3,4-tetrahydroisoquinoline;

(E)-6-Bromo-2-(4-(3-(6-indolylpropenoyl)amino)butyl)-1,2,3,4,-tetrahydroisoquinoline;

(E)-6-Chloro-2-(4-(3-(5-indolylpropenoyl)amino)butyl)-1,2,3,4,-tetrahydroisoquinoline;

(E)-6-Chloro-2-(4-(3-(2-naphythylpropenoyl)amino)butyl)-1,2,3,4-tetrahydroisoquinoline;

(E)-6-Bromo-2-(4-(3-(5-(3-methyl)indolylpropenoyl) aminobutyl)-1,2,3,4-tetrahydroisoquinoline;

(E)-6-Chloro-2-(4-(3-(6-indolylpropenoyl)amino)butyl)-1,2,3,4-tetrahydroisoquinoline;

(E)-2-(4-(3-(5-(3-Acetyl)indolylpropenoyl)amino)butyl)-6-bromo-1,2,3,4-tetrahydroisoquinoline;

(E)-6-Bromo-2-(4-(3-(6-(2-methyl)indolylpropenoyl) amino)butyl)-1,2,3,4-tetrahydroisoquinoline;

(E)-6-Bromo-2(4-(3-(5-(2-methyl)-1H-benzimidazolylpropenoyl)amino)butyl)-1,2,3,4-tetrahydroisoquinoline;

(E)-6-Bromo-2-(4-(3-(5-(1-methyl)indolylpropenoyl) amino)butyl)-1,2,3,4-tetrahydroisoquinoline;

2-(4-(4-(4-Actylphenyl)benzoylamino)butyl)-6-trifluoromethoxy-1,2,3,4-tetrahydroisoquinoline;

6-Methoxy-2-(4-(4-phenylbenzoylamino)butyl)-1,2,3,4-tetrahydroisoquinoline;

6-Hydroxy-2-(4-(4-phenylbenzoylamino)butyl)-1,2,3,4-tetrahydroisoquinoline;

2-(4-(4-phenylbenzoylamino)butyl)-6-trifluoromethylsulfonyloxy-1,2,3,4-tetrahydroisoquinoline;

or a salt thereof.

4. A process for preparing a compound of formula (I) or a salt thereof as defined in claim 1 which process comprises:

(a) reacting a compound of formula (II):

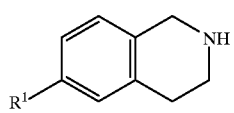

Formula (II)

wherein R¹ and q are as hereinbefore defined;

with a compound of formula (III):

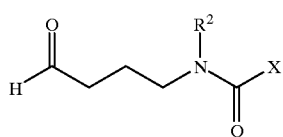

Formula (III)

wherein R² and X are as hereinbefore defined; or (b) reacting a compound of formula (IV):

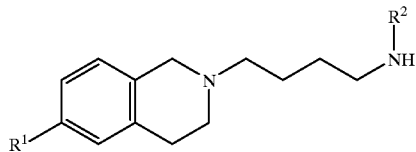

Formula (IV)

wherein $R^1$ and $R^2$ are as hereinbefore defined;
with a compound of formula (V):

XCOL   Formula (V)

wherein X is as hereinbefore defined and L is a halogen atom or the residue of an activated ester; or (c) preparing a compound of formula (I) wherein $R^1$ is $Ar^3$—Z and Z is a bond, reacting a compound of formula (VI):

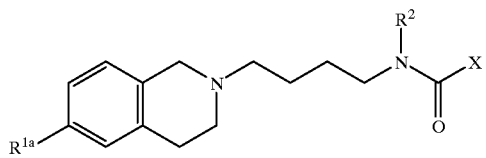

Formula (VI)

wherein $R^{1a}$ represents a group W wherein W is a halogen atom or a trifluoromethylsulphonyloxy group, or W is a group M selected from a boron derivative e.g. a boronic acid function $B(OH)_2$ or a metal function such as trialkylstannyl e.g. $SnBu_3$, zinc halide or magnesium halide; with a compound $Ar^3$—$W^1$, wherein $W^1$ is a halogen atom or a trifluoromethylsulphonyloxy group when W is a group M or $W^1$ is a group M when W is a halogen atom or a trifluoromethylsulphonyloxy group; or (d) preparing a compound of formula (I) wherein $R^1$ is $Ar^3$—Z and Z is O or S, reacting a compound of formula (VII):

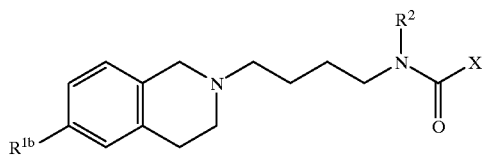

Formula (VII)

wherein $R^{1b}$ represents a group ZH; with a reagent serving to introduce the group $Ar^3$; or (e) preparing a compound of formula (I) where X represents the group —Ar—Y—$Ar^1$ and Y is a bond, reaction of a compound of formula (VIII):

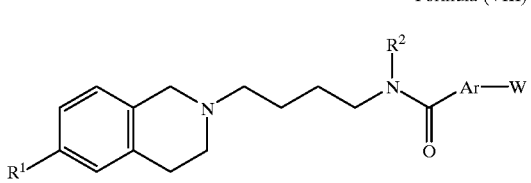

Formula (VIII)

wherein $R^1$, $R^2$, Ar and W are as hereinbefore defined, with a compound $Ar^1$—$W^1$, wherein $W^1$ is a halogen atom or a trifluoromethylsulphonyloxy group when W is a group M, or $W^1$ is a group M when W is a halogen atom or a trifluoromethylsulphonyloxy group; or (f) interconverting one compound of formula (I) to a different compound of formula (I);

and optionally thereafter forming a salt of formula (I).

5. A pharmaceutical composition comprising a compound of formula (I) as claimed in claim 1 or a physiologically acceptable salt thereof and a physiologically acceptable carrier therefor.

6. A method of treating a condition which requires modulation of a dopamine receptor which comprises administering to a subject in need thereof an effective amount of a compound of formula (I) as claimed in claim 1 or a physiologically acceptable salt thereof.

7. The method of claim 6, wherein the dopamine receptor is a dopamine $D_3$ receptor.

8. The method of claim 6, wherein the compound of formula (I) is a dopamine antagonist.

9. The method of claim 6, wherein the condition is a psychotic condition.

10. A pharmaceutical composition comprising a compound of formula (I) as claimed in claim 2 or a physiologically acceptable salt thereof and a physiologically acceptable carrier thereof.

11. A pharmaceutical composition comprising a compound of formula (I) as claimed in claim 3 or a physiologically acceptable salt thereof and a physiologically acceptable carrier thereof.

* * * * *